US008601185B2

(12) United States Patent
Sandhu et al.

(10) Patent No.: US 8,601,185 B2
(45) Date of Patent: Dec. 3, 2013

(54) SYSTEM AND METHODS FOR AVOIDING DATA COLLISIONS OVER A DATA BUS

(75) Inventors: Kulbir S. Sandhu, Fremont, CA (US); Atila G. Amiri, Fremont, CA (US); Samuel K. Gee, San Bruno, CA (US)

(73) Assignee: St. Jude Medical, Atrial Fibrillation Divison, Inc., St. Paul, MN (US)

( * ) Notice: Subject to any disclaimer, the term of this patent is extended or adjusted under 35 U.S.C. 154(b) by 248 days.

(21) Appl. No.: 12/982,441

(22) Filed: Dec. 30, 2010

(65) Prior Publication Data
US 2012/0017013 A1    Jan. 19, 2012

Related U.S. Application Data

(60) Provisional application No. 61/365,263, filed on Jul. 16, 2010.

(51) Int. Cl.
G06F 13/12    (2006.01)
G06F 13/00    (2006.01)

(52) U.S. Cl.
USPC .................. 710/61; 710/62; 710/72; 710/110

(58) Field of Classification Search
None
See application file for complete search history.

(56) References Cited

U.S. PATENT DOCUMENTS

| | | | | |
|---|---|---|---|---|
| 4,615,723 A | * | 10/1986 | Rodriguez-Fernandez et al. | 65/163 |
| 5,555,548 A | * | 9/1996 | Iwai et al. | 709/208 |
| 5,675,830 A | * | 10/1997 | Satula | 710/9 |
| 6,111,888 A | * | 8/2000 | Green et al. | 370/461 |
| 7,206,882 B2 | * | 4/2007 | White et al. | 710/110 |
| 7,296,312 B2 | * | 11/2007 | Menkedick et al. | 5/611 |
| 7,437,209 B2 | * | 10/2008 | Lachmann | 700/157 |
| 7,486,693 B2 | * | 2/2009 | Walter et al. | 370/437 |
| 7,587,541 B2 | * | 9/2009 | Chen et al. | 710/110 |
| 7,624,212 B2 | * | 11/2009 | Helmecke et al. | 710/72 |
| 7,769,427 B2 | * | 8/2010 | Shachar | 600/424 |
| 2003/0093460 A1 | * | 5/2003 | Kinney et al. | 709/202 |
| 2006/0088044 A1 | * | 4/2006 | Hammerl | 370/402 |
| 2008/0091193 A1 | * | 4/2008 | Kauphusman et al. | 606/41 |
| 2011/0241265 A1 | * | 10/2011 | Schmidt | 264/532 |

FOREIGN PATENT DOCUMENTS

WO    2010036746 A1    4/2010

OTHER PUBLICATIONS

"CANopen Application Layer and Communication Profile: CiA Draft Standard 301"; CAN in Automation (CIA) e. V.; Version 4.02; Feb. 13, 2002; pp. 17-19, 29-72.
Martin Rostan, "Configuration Guideline for CANopen Networks"; CAN in Automation; iCC 2003; pp. 04-07 through 04-13.
"CANopen Hands-On Tutorial"; Embedded Systems Academy; Feb. 2008; slides 11-18, 34-57.

* cited by examiner

*Primary Examiner* — Henry Tsai
*Assistant Examiner* — Jing-Yih Shyu
(74) *Attorney, Agent, or Firm* — Dykema Gossett PLLC

(57) ABSTRACT

The disclosed system and methods involve controlling the timing and order in which numerous motors and sensors exchange data over a data bus. The method can be used with, for example, motion control, automotive, industrial automation, and medical equipment applications using data buses. As an example of one possible medical equipment application, the method of exchanging data on a bus can be used with a remote catheter guidance system. The disclosed system and methods help optimize data exchange over a bus and avoid collisions by grouping the transmission of sensor readings, by grouping the transmission of motor commands, and by predetermining the order of these groups. Further, the method provides a way of ensuring that incomplete data sets are not exchanged over the bus. The method also provides a way of synchronizing motor actuation based on data transmitted to the data bus.

22 Claims, 13 Drawing Sheets

SYSTEM AND METHODS FOR AVOIDING DATA COLLISIONS OVER A DATA BUS

CROSS-REFERENCE TO RELATED APPLICATIONS

This application claims the benefit of U.S. provisional application No. 61/365,263, filed 16 Jul. 2010, which is hereby incorporated by reference as though fully set forth herein.

BACKGROUND OF THE INVENTION a. Field of the Invention

The present disclosure relates generally to a data bus collision avoidance system and methods that efficiently and effectively transmit data to and receive data from a data bus, and more particularly to a data bus system and methods that provide for the reliable exchange of data between components of a remote catheter guidance system.

b. Background Art

Many electrical, electronic and mechanical systems utilize components that cooperate or work together by exchanging data, often over a data bus. As these systems grow in complexity, the need to exchange this data orderly, efficiently, reliably, and predictably over the data bus increases. Often, the proper operation of these systems are dependent on the precise transmission of control commands and sensor information.

In particular, as medical systems progress to provide more control of instruments like catheters, so too must the means of communicating between components of those medical systems. Data buses are used to exchange data between multiple devices, which are connected to the data buses through nodes, which operably connect devices to the data bus.

In one type of medical procedure, a catheter is manipulated through a patient's vasculature to a patient's heart, and carries one or more electrodes which can be used for mapping, ablation, diagnosis, or other treatments. Once at the intended site, treatment can include ablation, cryoablation, lasers, chemicals, high-intensity focused ultrasound, etc. As readily apparent, such treatment requires precise control of the catheter during manipulation to, from, and at the treatment site. This can be accomplished by the effective and reliable transmission of data and return of sensor information.

Problematic data collisions occur when more than one node attempts to access the same node or physical media at the same time. The electrical signals from different nodes cannot coexist in the same physical media at the same time and remain intelligible. Collisions can cause missed input and output cycles, errors in transmitting data and reading data, and, in turn, unexpected system performance.

Many current solutions to the problem of bus collision involve attempts to re-transmit data through a number of retries. These solutions add overhead and delays in the system to achieve data transmission. Other solutions attempt to prioritize nodes in a hierarchy. These solutions unnecessarily complicate the system, make configuration and reconfiguration difficult, and add overhead—especially where the system needs to maintain priority directories on a dynamic basis.

The inventors herein have thus recognized a need for a data bus that can perform efficient yet accurate data exchange between the various components of a system.

BRIEF SUMMARY OF THE INVENTION

One advantage of the system and methods described, depicted, and claimed herein relate to the reliable and efficient exchange of data over a data bus in a system having multiple components.

The disclosure is directed to a data bus collision avoidance system and methods for controlling operations on a data bus used to transmit motor commands to and receive sensor readings from the components of a system. In particular, the data bus collision avoidance system and methods are described as used with a remote catheter guidance system. The system can include an electronic control system and a memory coupled to the electronic control system. Control logic is stored within the memory and is configured to be executed by the electronic control system. The electronic control system can control the transmission of motor commands to the data bus for further distribution to components such as motors ready to actuate upon those commands. The electronic control system can also control the transmission of sensor readings from components such as sensors.

In various embodiments, an input/output (IO) cycle on the data bus can involve motor operations, sensor operations, or both motor and sensor operations. In an embodiment involving motor operations, an electronic control system can provide motor commands to the data bus. Thereafter, a synchronization signal can prompt the motors to actuate upon these motor commands at the same time. This simultaneous actuation allows for coordinated motion, thereby reducing any possible erratic or semi-erratic motion from the motors. In an embodiment involving both motor and sensor operations, the data bus or a mechanism associated therewith can retrieve the sensor reading from each sensor one at a time after actuation of the motors. Once the data bus has received all of the sensor information or readings, the electronic control system or other components of the system can read the sensor information from the data bus. Further, since not every component needs to exchange data as frequently as others, more critical components can exchange data during IO cycles that recur more frequently. Less critical components can exchange data during IO cycles that recur less frequently. By providing order to the way in which data is exchanged, the reliability and efficiency of the data bus is improved.

The foregoing and other aspects, features, details, utilities, and advantages of the present invention will be apparent from reading the following description and claims, and from reviewing the accompanying drawings.

DETAILED DESCRIPTION OF THE INVENTION

As described above, a data bus system and related methods are disclosed for providing more efficient and reliable exchange of data over a data bus and thereby reducing or eliminating data collisions or transmission errors. Such a data bus system and methods can be used in numerous applications that have need for the transmission of control commands and that receive sensor information. However, before proceeding to a detailed description of the data bus collision avoidance system, a brief overview, for context purposes, of an exemplary remote catheter guidance system (RCGS) for manipulating a medical device will first be described. The disclosed data bus system and methods are particularly applicable to such a system and the description of the RCGS will detail the need for efficient transmission of control commands and sensor information for a more effective use of the RCGS system. After the description of the RCGS, the present specification will then provide a description of the data bus technology and how it can be used in the RCGS.

Figure 1:
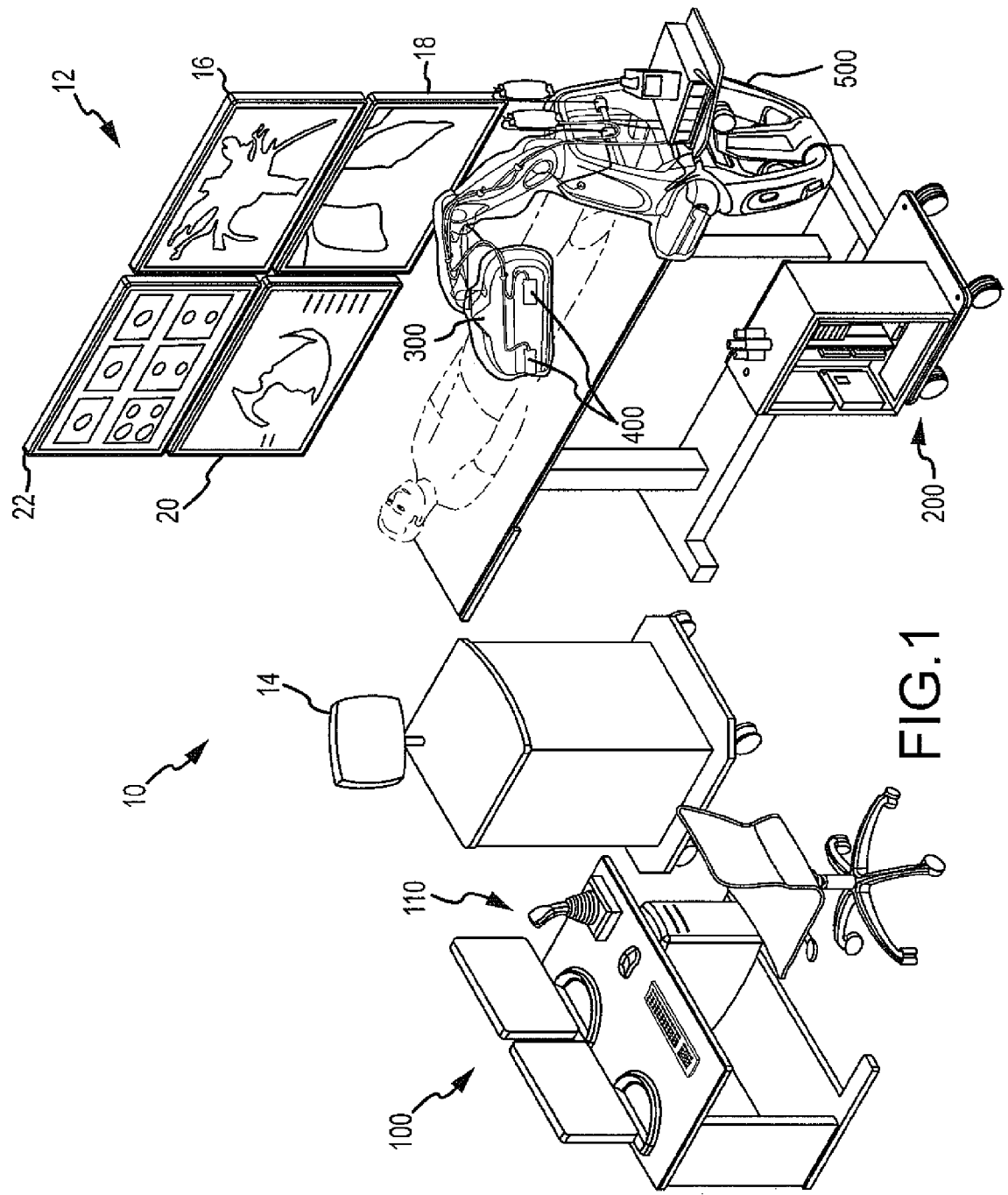
FIG. 1 is an isometric diagrammatic view of a remote catheter guidance system, illustrating an exemplary layout of various system components.

Now referring to the drawings wherein like reference numerals are used to identify identical components in the various views, FIG. 1 is a diagrammatic view of an exemplary RCGS 10, in which several aspects of a system and methods for avoiding collisions of data on a data bus can be used.

Exemplary RCGS System Description. The RCGS 10 can be likened to power steering for a catheter system. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target position, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, and a manipulator support structure 500 for positioning the manipulator assembly 300 in proximity to a patient or a patient's bed.

Displays 12 are configured to visually present to a user information regarding patient anatomy, medical device location or the like, originating from a variety of different sources. Displays 12 can include (1) an ENSITE VELOCITY monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) an EP recording system display 22.

The system 14 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an ENSITE VELOCITY system running a version of NavX software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. System 14 can comprise conventional apparatus known generally in the art, for example, the ENSITE VELOCITY system described above or other known technologies for locating/navigating a catheter in space (and for visualization), including for example, the CARTO visualization and location system of Biosense Webster, Inc., (e.g., as exemplified by U.S. Pat. No. 6,690,963 entitled "SYSTEM FOR DETERMINING THE LOCATION AND ORIENTATION OF AN INVASIVE MEDICAL INSTRUMENT" hereby incorporated by reference in its entirety), the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. Nos. 7,536,218, and 7,848,789 both of which are hereby incorporated by reference in its entirety). Some of the localization, navigation and/or visualization systems can involve providing a sensor for producing signals indicative of catheter location and/or orientation information, and can include, for example one or more electrodes in the case of an impedance-based localization system such as the ENSITE VELOCITY system running NavX software, which electrodes can already exist in some instances, or alternatively, one or more coils (i.e., wire windings) configured to detect one or more characteristics of a low-strength magnetic field, for example, in the case of a magnetic-field based localization system such as the gMPS system using technology from MediGuide Ltd. described above.

The input control system 100, which can include a joystick 110 for allowing a user to control a catheter, is configured to allow a user, such as an electrophysiologist, to interact with the RCGS 10, in order to control the movement and advancement/withdrawal of both a catheter and sheath (see, e.g., commonly assigned U.S. patent application Ser. No. 12/751,843 filed Mar. 31, 2010 entitled "ROBOTIC CATHETER SYSTEM" and PCT/US2009/038597 entitled "ROBOTIC CATHETER SYSTEM WITH DYNAMIC RESPONSE", published as WO 2009/120982; the entire disclosure of both applications being hereby incorporated by reference). Generally, several types of input devices and related controls can be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, commonly assigned U.S. patent application Ser. No. 12/933,063 entitled "ROBOTIC CATHETER SYSTEM INPUT DEVICE" and U.S. patent application Ser. No. 12/347,442 entitled "MODEL CATHETER INPUT DEVICE", the entire disclosure of both applications being hereby incorporated by reference. The input devices can be configured to directly control the movement of the catheter and sheath, or can be configured, for example, to manipulate a target or cursor on an associated display.

The electronic control system 200 is configured to translate (i.e., interpret) inputs (e.g., motions) of the user at an input device or from another source into a resulting movement of the catheter and/or surrounding sheath. In this regard, the system 200 includes a programmed electronic control unit (ECU) in communication with a memory or other computer readable media (memory) suitable for information storage. Relevant to the present disclosure, the electronic control system 200 is configured, among other things, to issue commands (i.e., actuation control signals) to the manipulator assembly 300 (i.e., to the actuation units—electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in commonly assigned U.S. patent application Ser. No. 12/751,843 filed Mar. 31, 2010 entitled "ROBOTIC CATHETER SYSTEM", described above. It should be understood that although the exemplary ENSITE VELOCITY system 14 and the electronic control system 200 are shown separately, integration of one or more computing functions can result in a system including an ECU on which can be run both (i) various control and diagnostic logic pertaining to the RCGS 10 and (ii) the visualization, mapping and navigation functionality of system 14.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly can be found in commonly assigned U.S. patent application Ser. No. 12/347,826 titled "ROBOTIC CATHETER MANIPULATOR ASSEMBLY", the entire disclosure of which is hereby incorporated by reference.

A device cartridge 400 is provided for each medical device controlled by the RCGS 10. For this exemplary description of an RCGS, one cartridge is associated with a catheter and a second cartridge is associated with an outer sheath. The cartridge is then coupled, generally speaking, to the RCGS 10 for subsequent robotically-controlled movement. In addition to the description set forth herein, further details of a device cartridge can be found in commonly owned U.S. patent application Ser. No. 12/347,835 entitled "ROBOTIC CATHETER DEVICE CARTRIDGE" and U.S. patent application Ser. No. 12/347,842 "ROBOTIC CATHETER ROTATABLE DEVICE CARTRIDGE", the entire disclosure of both applications being hereby incorporated by reference.

Figure 2:
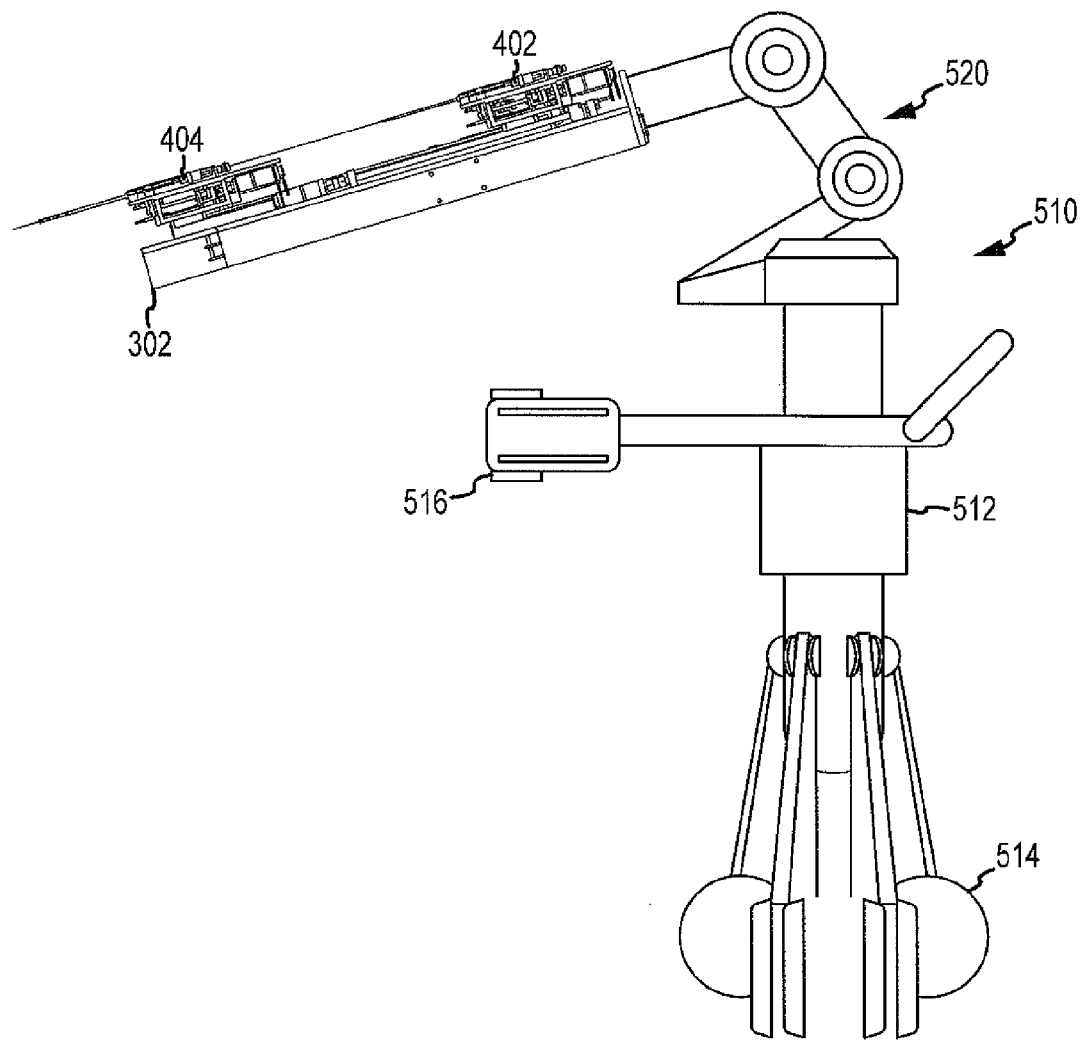
FIG. 2 is a side view of a manipulator assembly shown in FIG. 1, coupled to a robotic support structure, showing side views of catheter and sheath manipulation mechanisms.

FIG. 2 is a side view of an exemplary robotic catheter manipulator support structure, designated structure 510 (see commonly owned U.S. patent application Ser. No. 12/347,811 entitled "ROBOTIC CATHETER SYSTEM" described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 3A:
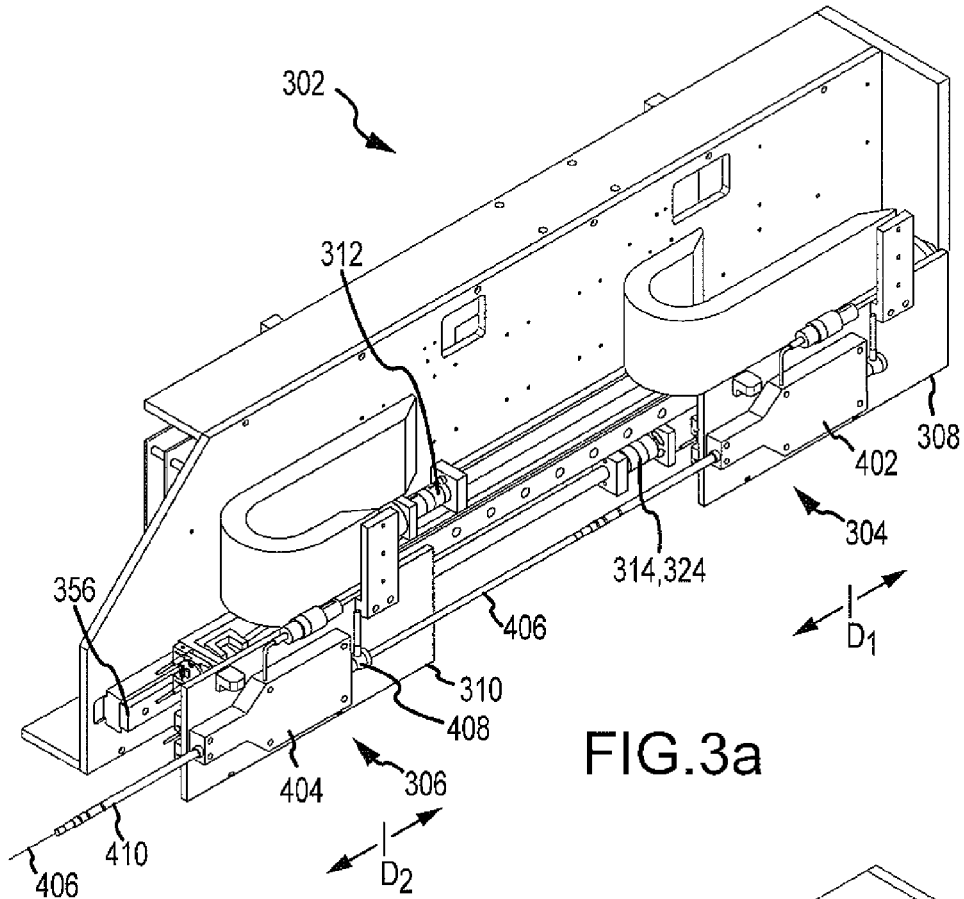
FIGS. 3a-3b are isometric views of a manipulator assembly shown in FIG. 2, showing the catheter and sheath manipulation mechanism in greater detail.
Figure 3B:
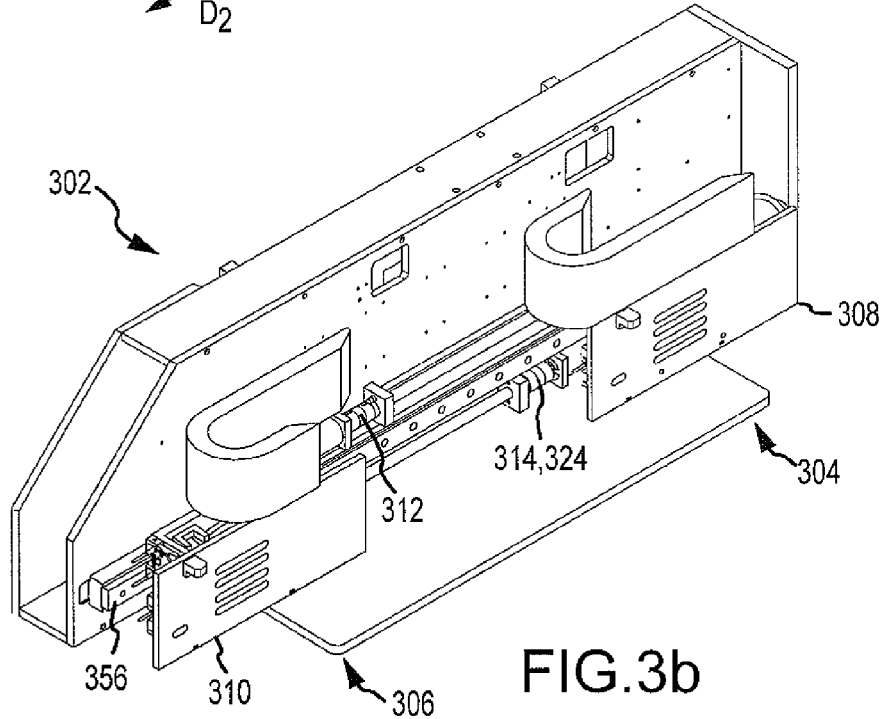
Figure 4A:
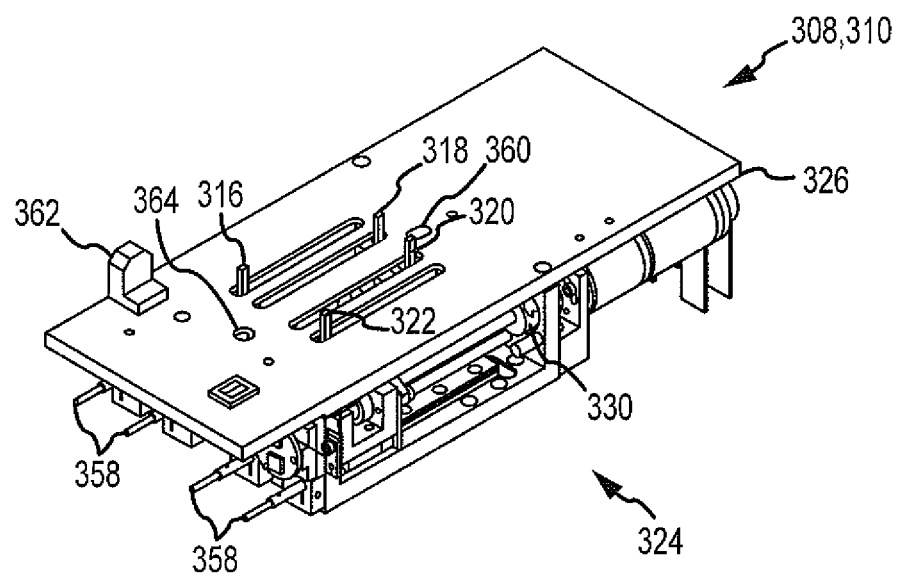
FIGS. 4a-4c are isometric views showing a sheath manipulation base of FIGS. 3a-3b in greater detail.
Figure 4B:
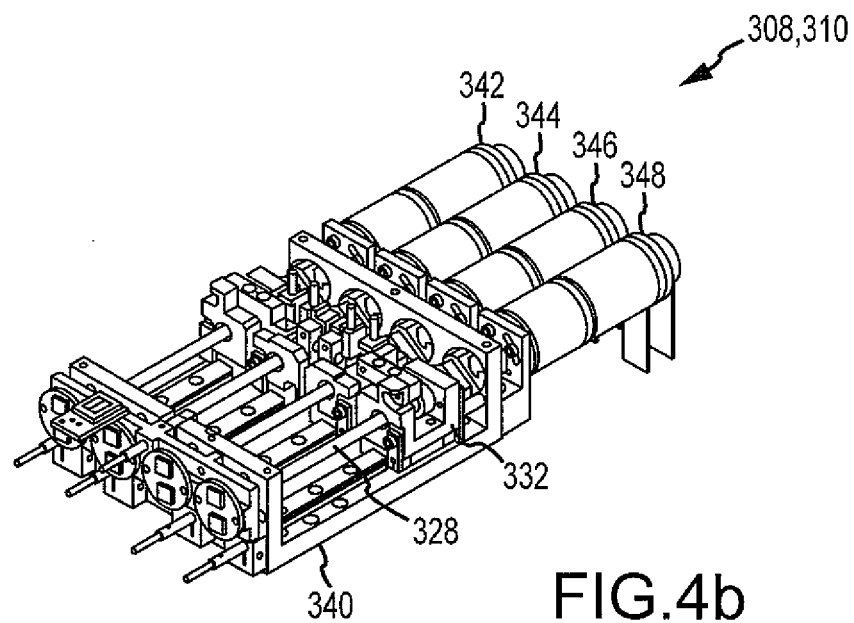
Figure 4C:
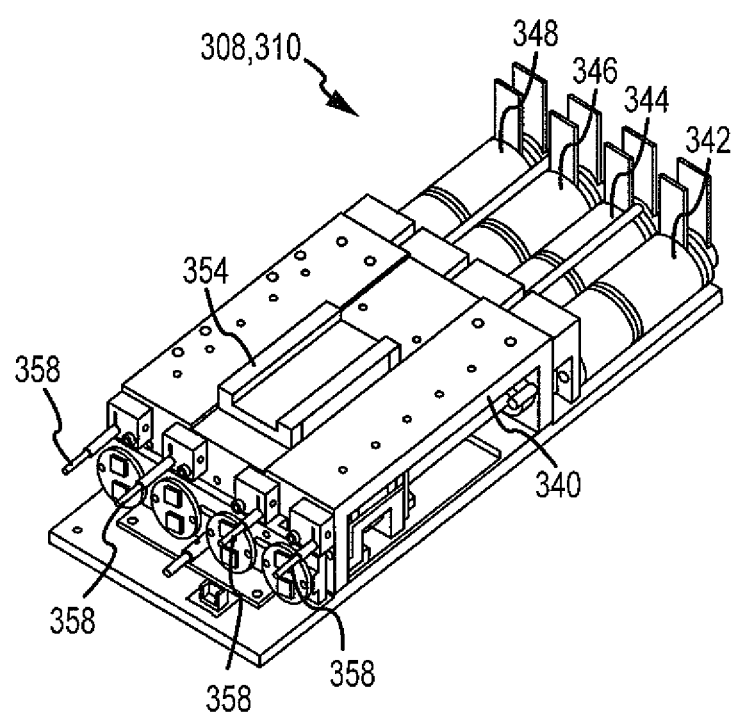
Figure 5A:
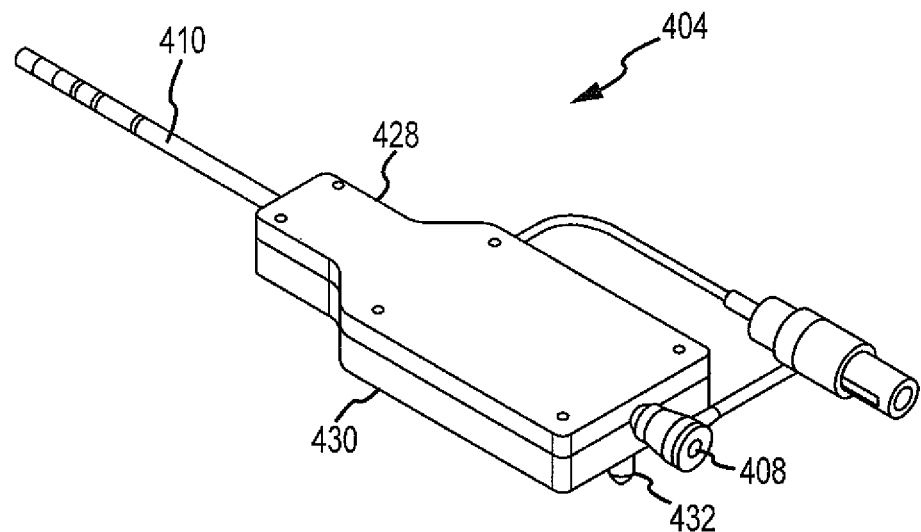
FIGS. 5a-5b are isometric views showing a sheath cartridge of FIGS. 3a-3b in greater detail.
Figure 5B:
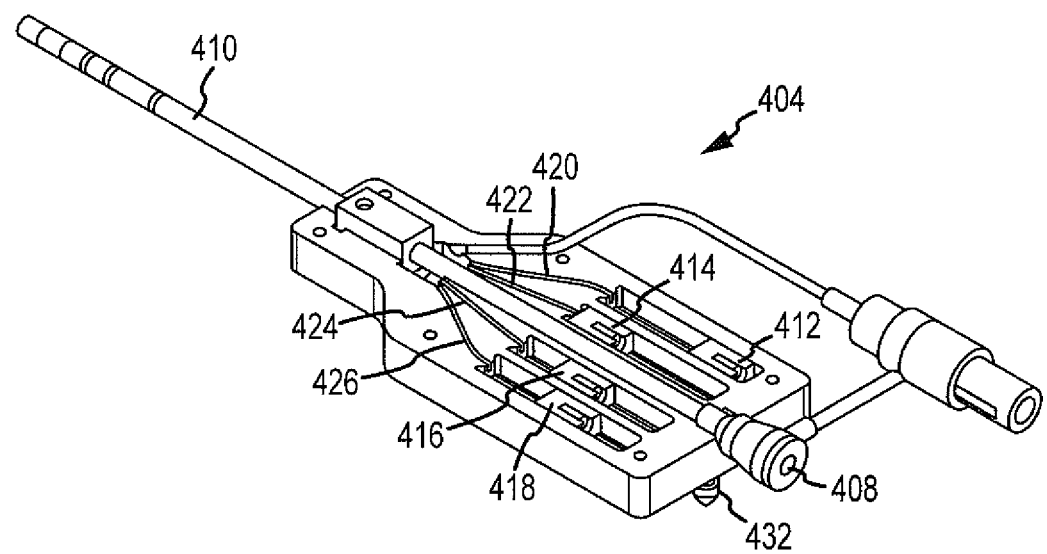

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597 entitled "ROBOTIC CATHETER SYSTEM WITH DYNAMIC RESPONSE", published as WO 2009/120982.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks (i.e., such as slider blocks 412, 414, 416, 418 are best shown in FIG. 5b) to independently tension select steering wires 420, 422, 424, 426 (also best shown in FIG. 5b). Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324 (best shown in FIG. 4a, i.e., for both finger control and for cartridge translation control, can further include encoders to measure a relative and/or an absolute position of each element of the system. Moreover, each motor-driven ball screw 324 (i.e., for both finger control and cartridge translation control) can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. These and other types of remote actuation can directly benefit from the teaching of the instant disclosure.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (i.e., four) steering wires. Device cartridges 402, 404 can be provided as a disposable item that is capable of being easily positioned (e.g., snapped) into place (i.e., onto a respective base 408, 410). Sheath cartridge 404 can be designed in a similar manner as the catheter cartridge 402, but will typically be configured to provide for the passage of catheter 406.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 10.

Figure 6:
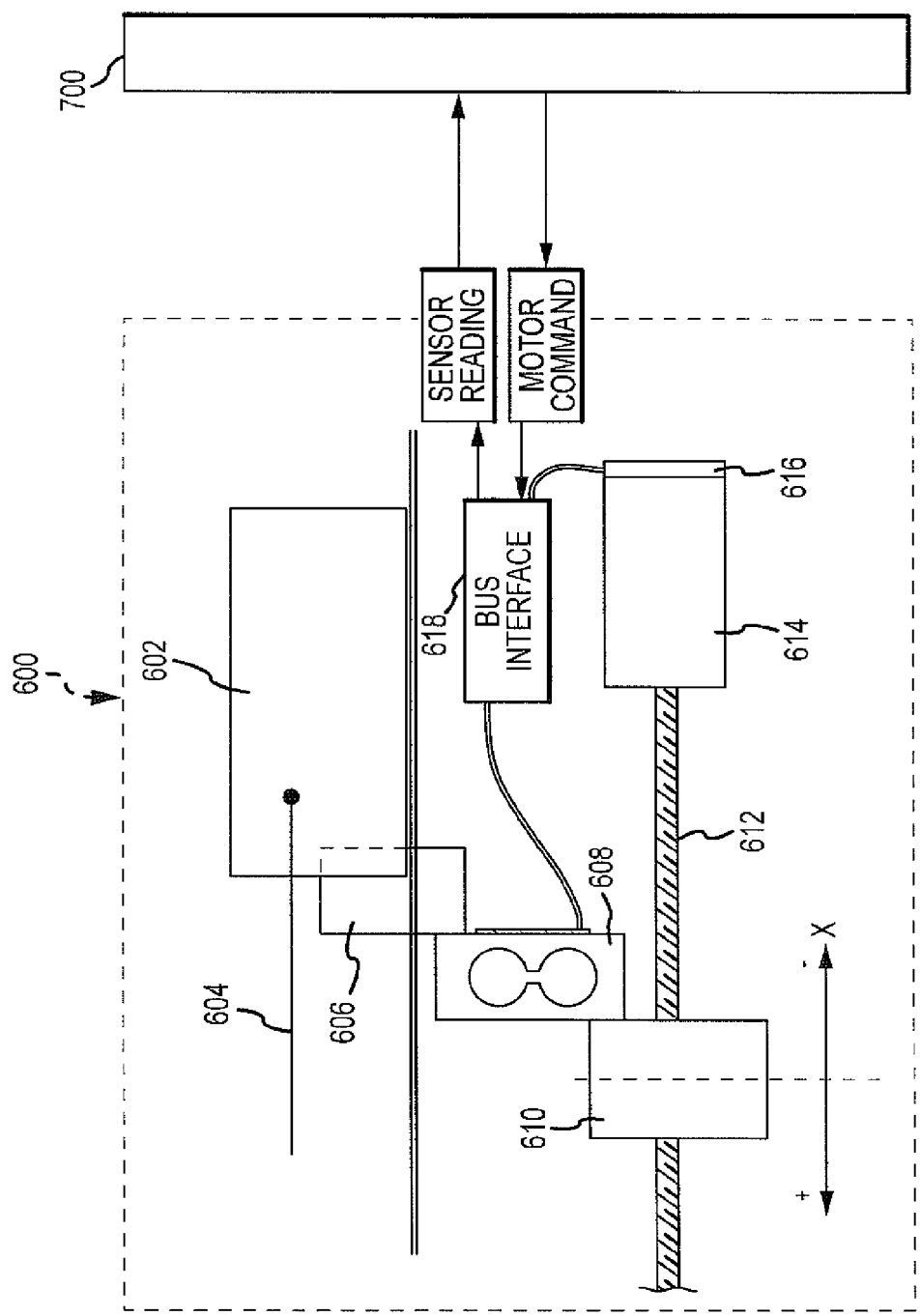
FIG. 6 is a diagrammatic view of the sheath manipulation mechanism of FIG. 2.

FIG. 6 is a diagrammatic view of a node suitable for connection to a communications or data bus 700 in the RCGS 10. The node includes an actuation unit 600, similar to the actuation mechanisms described above (e.g., catheter actuation mechanism 304). The RCGS 10 can have at least ten such actuation units (i.e., one for each of the four catheter steering wires, four sheath steering wires, one catheter manipulation base and one sheath manipulation base), which as described include electric motors. Operations on the data bus 700 used to transmit data to and receive data from the actuation unit 600 are scheduled so that the actuation unit 600 can exchange data reliably and predictably.

FIG. 6 shows in diagrammatic or block form many of the components described above—where appropriate, references to the earlier describe components will be made. Actuation unit 600 includes a first, slidable control member 602 (i.e., slider as described above) that is connected to or coupled with a second, tensile control member 604 (i.e., steering wire as described above). The slider 602 can be configured to interface with a third, movable control member 606 (i.e., finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 can also include a rotary motor position encoder 616 that is coupled to the motor 614 and is configured to produce a signal indicative of the position of the motor 614. The encoder 616 can comprise an internal, optical encoder assembly, integral with motor 614, configured to produce a relatively high accuracy signal. The motor position sensor can operate in either absolute or relative coordinates. In an embodiment, a second motor position sensor (not shown) can also be provided, such as a potentiometer (or impedance-based), configured to provide a varying voltage signal proportional to the motor's rotary position. The signal of the secondary position sensor can be used as an integrity check of the operating performance of the primary position sensor (encoder) during start-up or initialization of the actuation unit.

Actuation unit 600 can also include one or more local controllers including a bus interface 618 to facilitate exchange of information between actuation unit 600 and electronic control system 200 or the ECU via the data bus 700. The local controller communicates with the main electronic control system 200 via the bus interface and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200.

Figure 7:
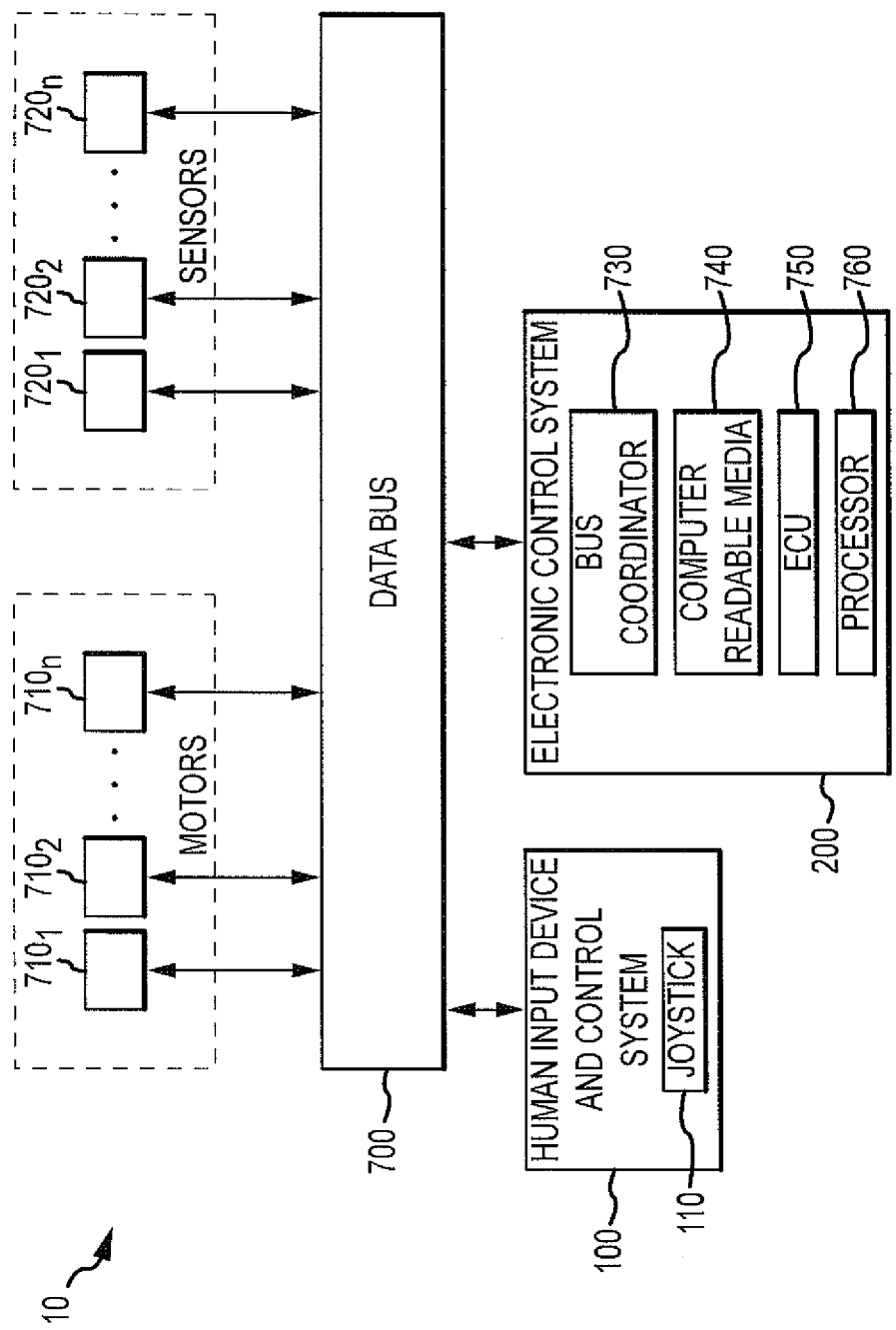
FIG. 7 is a schematic diagram showing several exemplary components between which a data bus can exchange data.

Data Bus Collision Avoidance in the RCGS Environment. Although motors, sensors, actuation units, cartridges, and various other components have been described with some detail, such descriptions serve merely to provide an environment in which to describe a system and methods for operating the data bus 700, as shown in FIG. 7.

It is contemplated that the data bus 700 can exchange data between many or even all components and subcomponents of a system that produce input data for or receive output data from an electronic control system. One example of such a component is the actuation unit 600, as shown in FIG. 6, which has several subcomponents. The data bus 700 can exchange data (i.e., both transmit data and receive data) in a system that includes many mechanical, electrical, electromechanical, and computer-based components. While components producing input data or receiving output data can conceivably include a vast array of components, for sake of simplicity, the following description refers to such components simply in terms of "motors" (requiring output) and "sensors" (producing input).

For a system with many components to function properly, its components must be capable of exchanging data predictably, reliably, and efficiently between and amongst one another. Therefore, the components of a system can transmit and receive data in a controlled manner by way of the data bus 700. Examples of the types of data that a system can exchange over the data bus 700 can include without limitation motor commands such as position, velocity, or acceleration; error conditions; sensor readings; and various other inputs and outputs.

In one embodiment, the system utilizing the data bus 700 can be the RCGS 10. As part of the RCGS 10, the electronic control system 200 can transmit motor commands to a plurality of motors 710 of the RCGS 10 over the data bus 700. The electronic control system 200 can also receive sensor readings from a plurality of sensors 720 of the RCGS 10 over the data bus 700. Still further, the electronic control system 200 can exchange data with the human input device and control system 100, which can include the joystick 110 for receiving input from a user. The electronic control system 200, described in more detail above, can include, for example, a bus controller 730, computer readable media 740, an ECU 750, and a processor 760. Since the electronic control system 200 controls the movement of the catheter and/or surrounding sheath, it follows that the electronic control system 200 can be configured to compute motor commands and receive and process sensor readings.

Various motors, such as the motor 614 of the actuation unit 600, can receive motor commands from the electronic control system 200 via the data bus 700. One exemplary motor command that can be transmitted over the data bus 700 can involve the catheter and sheath manipulator mechanisms 304, 306 imparting translational movement to the catheter 406 and the sheath 410. Also, various sensors of the RCGS 10 can transmit sensor readings back to the electronic control system 200 over the data bus 700. An exemplary sensor reading can include a strain gauge measuring steering wire tension. Another exemplary sensor reading can involve the encoder 616 measuring the position of the motor 614 in FIG. 6.

In some embodiments, it is contemplated that the electronic control system 200 computes the motor commands at least in part in response to the sensor readings. In other words, the sensor readings can serve as a form of closed-loop feedback for the RCGS 10. For example, if the encoder 616 measures that the motor 614 is not in its expected position, the electronic control system 200 can use this information to generate a motor command that compensates for this discrepancy. During the next cycle that the motor 614 is scheduled to receive a motor command, the electronic control system 200 can provide the motor 614 with the compensatory motor command.

Generally, motors and sensors can be operably connected to the data bus 700 at representative nodes, such as that shown by the actuation unit 600 in FIG. 6. More specifically, motors and sensors can interface with the data bus 700 by way of a bus interface, such as the bus interface 618 shown in FIG. 6.

The bus interface 618 can be configured to fetch data from the data bus 700, typically through some device driver. The bus interface 618 can also be configured to perform sampling of input data periodically. As shown and described, a node can be configured to accommodate the data exchange for more than one component or subcomponent, such as an encoder sensor and a motor. Moreover, nodes can include components and subcomponents other than those shown in FIG. 6. For example, nodes can have an associated local memory, or more generally, a local "buffer," in which data values are stored, in some cases, temporarily. In some embodiments, there can be a local buffer for each motor or sensor of a node. In other embodiments, there can be a shared local buffer. In yet other embodiments, the bus interfaces can contain the local buffer(s). In still further embodiments, the local buffer can even be at or on the data bus 700. In other embodiments, however, a local buffer is not necessary.

One aspect of the data bus 700 can involve broadcasting. A component node operably connected to the data bus 700 can transmit or "broadcast" data to more than one or even all other nodes connected to the data bus 700. For example, the electronic control system 200 or the bus controller 730 can broadcast a startup message system-wide, that is, to all of the nodes connected to the data bus 700. However, nodes can be tuned to "listen" only to the transmissions of certain other nodes. For example, the motors of the RCGS 10 that control the steering wires can be tuned to listen only to the node or nodes corresponding to the electronic control system 200. Thus the motors would not listen to data transmissions directly from the sensors of RCGS 10. On the other hand, the electronic control system 200 can be tuned to listen to the input from the sensors of the RCGS 10.

Generally, the bus controller 730 can be responsible for overseeing the operations of the data bus 700. More specifically, the bus controller 730 can include at least one program, algorithm, control logic, memory, and/or the like for scheduling, timing, and/or coordinating access to the data bus 700. The processor 760 of the electronic control system 200 can execute a program or the like of the bus controller 730. In one embodiment, the bus controller 730 can be based on a standard called CANopen. CANopen relates to the application layer of the OSI/ISO layer model, and one objective of CANopen is to control how data buses exchange real-time process data. In another exemplary embodiment, the bus controller 730 can be based on a general purpose input output (GPIO) standard. In yet other embodiments, the bus controller 730 can be based on a serial peripheral interface (SPI) bus standard. Furthermore, as shown in FIG. 7, the bus controller 730 can be part of the electronic control system 200 in one embodiment. In another embodiment, however, the bus controller 730 can be separate and distinct from the electronic control system 200.

To optimize usage of the data bus 700 and to minimize bus traffic, the bus controller 730 can be programmed to schedule data exchanges on the data bus 700 in predetermined sequences of input/output (IO) cycles. An IO cycle can involve transmitting over the data bus 700 at least one motor command to at least one motor and actuating the motor(s) based on the motor command(s). These events can be referred to collectively as motor "operations." On the other hand, an IO cycle can involve receiving, retrieving, obtaining, sampling, acquiring, or otherwise collecting at least one sensor reading from at least one sensor and transmitting over the data bus 700 the sensor reading(s) to the electronic control system 200 and other interested components. These events can be referred to collectively as sensor "operations." Further, an IO cycle can involve performing both motor operations and sensor operations.

Figure 8:
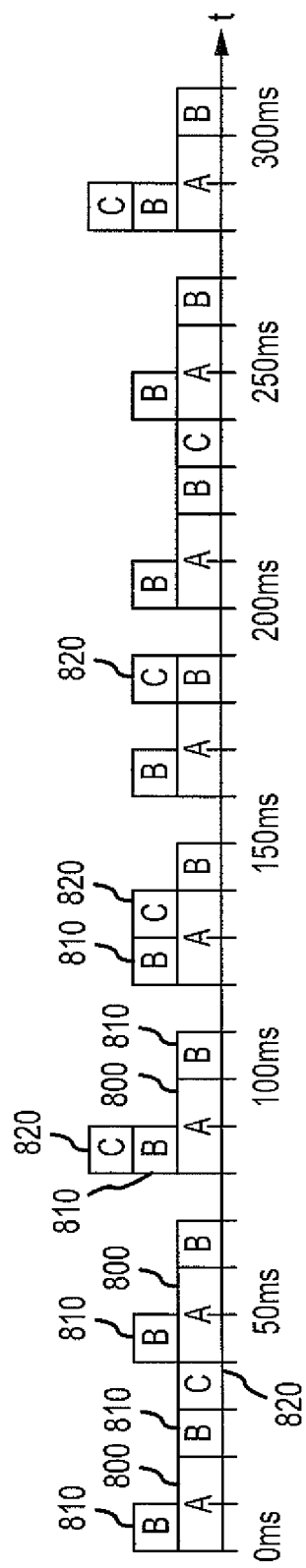
FIG. 8 is a general timeline showing how access to a data bus can be allocated between recurring input/output cycles.

As shown by the exemplary bus access timeline in FIG. 8, the bus controller 730 can be programmed to schedule IO cycles in predetermined sequences. IO cycles can recur at different frequencies such that some IO cycles can have a shorter cycle period than other IO cycles. Moreover, IO cycles can have different cycle durations such that some IO cycles take longer to complete than other IO cycles. For example, IO cycle-A 800 in FIG. 8 has a cycle period of 40 milliseconds and a cycle duration of 20 milliseconds. This means that IO cycle-A 800 performs its list (or "thread") of operations when a cycle timer specific to IO cycle-A 800 expires every 40 milliseconds. This also means that IO cycle-A is allotted 20 milliseconds of bus access time to complete its thread of operations. The cycle timer for each IO cycle can be defined when the bus controller 730 is programmed. IO cycle-B 810, on the other hand, has a cycle period of 20 milliseconds and a cycle duration of 10 milliseconds. This means that IO cycle-B 810 recurs every 20 milliseconds and is allotted 10 milliseconds of bus access time to complete its thread of operations. Further, IO cycle-C 820 has a cycle period of 50 milliseconds and a cycle duration of 10 milliseconds to complete its thread of operations.

It should be noted that FIG. 8 is merely exemplary. The RCGS 10 can have more or considerably more than three IO cycles, some of which can have IO cycle periods in the range of one or more seconds. Moreover, IO cycle periods and IO cycle durations need not be in 10 millisecond increments. Although FIG. 8 shows some instances where multiple IO cycles start performing operations at the same time, such as between 0-10, 40-50, and 80-90 milliseconds, there can be some instances where multiple IO cycles do not start at the same time. For example, one IO cycle can be halfway completed when another IO cycle is scheduled to begin.

Components of the RCGS 10 that produce input data or receive output data (IO components) can be assigned to the thread of a specific IO cycle based on need for data in the RCGS 10. Need for data can involve determining the frequency with which each IO component should have access to the data bus 700. Hence critical components, which have a high need for data or that produce data for which the electronic control system 200 has a high need, can be assigned to IO cycles that recur more frequently. This would allow more critical components to perform operations via the data bus 700 more frequently than less critical components. Also, it can be advantageous in some embodiments to group and assign motors performing similar functions to the same IO cycle. Likewise, it can be advantageous to group and assign sensors measuring similar attributes of the RCGS 10 to the same IO cycle.

One example of a critical component is the motor 614 shown in FIG. 6, which ultimately controls the steering wire 604. The motor 614 could be assigned to IO cycle-B 810, which has a relatively short cycle period of 20 milliseconds. Another example of a critical component that deserves frequent data exchange can be sensors instrumented throughout the human input device and control system 100. Some of these sensors can measure the deflection of the joystick 110 caused by a user desiring to manipulate the catheter 406. These sensor readings provide input to the electronic control system 200, which in turn computes motor commands based on those sensor readings. By contrast, a less critical component, such as a motor driving a fan blowing air over the electronic control system 200, could be assigned to an IO cycle that only recurs once every second.

IO cycles can communicate with the data bus 700 at mutually exclusive points in time. However, as mentioned above, instances can occur in which more than one IO cycle requires common access to the data bus 700. FIG. 8 shows several of these instances at time periods represented at 0-10, 40-50, 80-90, 120-140, and 160-170 milliseconds, and so on. Yet before an IO cycle can perform its thread of IO operations, it must acquire "mutex" (based on principles of mutual exclusion) to write to and read from a buffer of the data bus 700. One way to reduce instances where different IO cycles are competing for mutex is by predetermining and spreading out the bus load, which is the general amount of activity occurring on the data bus 700 at any given time. Furthermore, through iterative programming of the bus controller 730 and testing of the RCGS 10 and the data bus 700, these instances can be minimized or even eliminated completely if desired.

Where these instances of competition for mutex are not eliminated completely, several techniques can be used to help ensure that data is still exchanged reliably and efficiently over the data bus 700. First, where two IO cycles desire mutex starting at the same time, the bus controller 730 can utilize a principle of priority inheritance mutex. Priority inheritance mutex means that the IO cycle with the higher priority will acquire mutex first, enabling the higher priority IO cycle to perform its operations first. One way for the bus controller 730 to determine priority is based on the cycle period of the IO cycle. Hence the IO cycle-B 810 in FIG. 8 would have priority over IO cycle-A 800 and IO cycle-C 820 since IO cycle-B 810 has the shortest cycle period (i.e., 20 milliseconds). Second, once a high priority IO cycle has acquired mutex and is performing operations on the data bus 700, the bus controller 730 can lock out or block lower priority IO cycles from using the data bus 700. Third, another scenario is presented where a lower priority IO cycle has mutex and is performing its operations when a higher priority IO cycle requests access to the data bus 700. Here, instead of suspending the lower priority IO cycle, the RCGS 10 can allocate more system resources to accelerate performance of the lower priority IO cycle. In turn, this still provides the higher priority IO cycle with prompt access to the data bus 700.

The IO cycle(s) is terminated at the end of its cycle duration regardless of whether the entire thread of operations are completed during an IO cycle and regardless of whether all IO cycles are able to access the data bus 700 during a given time period. IO cycles are terminated at the end of their cycle durations because the predetermined sequence for bus access time must continue. As a result, the electronic control system 200 can be left to compensate for the effects of any missed IO cycles. As a preventative measure, though, during testing of the data bus 700 with a particular system, it can be determined whether the system can tolerate certain operations that are missed on occasion. If the system can tolerate these missed operations, then the bus controller 730 need not be reprogrammed. If the system cannot tolerate these missed operations, the bus controller 730 can be reprogrammed such that these operations are not missed.

In addition to providing order to the sequence of IO cycles, the bus controller 730 can also provide order to the operations performed within IO cycles. Providing order within the IO cycle can help reduce collisions and the duration of IO cycles.

Figure 9:
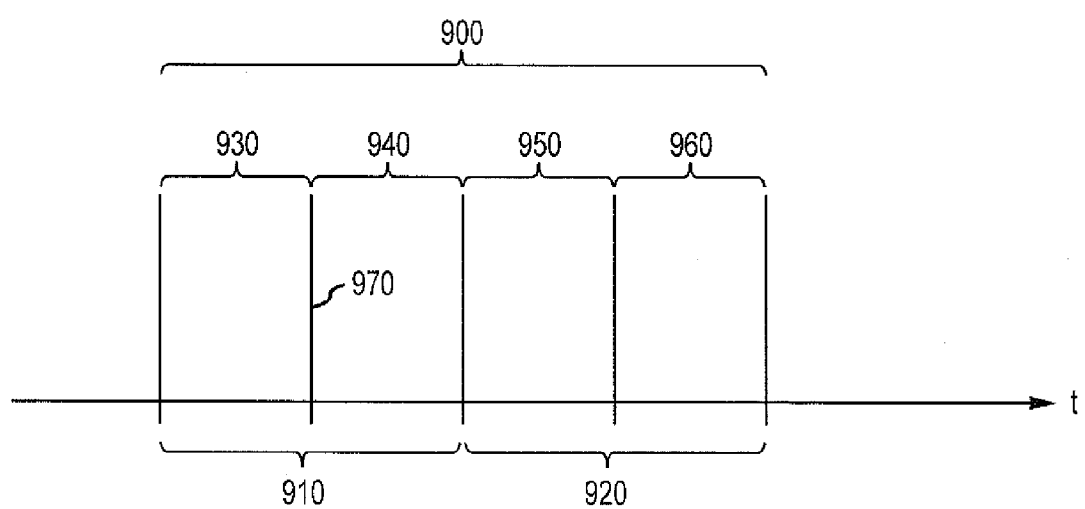
FIG. 9 is a timeline showing intervals and subintervals of an exemplary input/output cycle.

FIG. 9 shows several examples of how the bus controller 730 can provide order within IO cycles. One example of how the bus controller 730 can provide order within an IO cycle pertains to IO cycles 900 involving both motor and sensor operations. In such an IO cycle 900, the bus controller 730 can be programmed so that motor operations are grouped together and performed during a motor time interval 910 that occurs before a sensor time interval 920 for performing sensor operations. Sensor operations can be grouped separately from motor operations, and sensor operations can be performed in the sensor time interval 920 occurring after the motor time interval 910. In the context of the RCGS 10, IO cycle 900 can be explained as data flowing from the electronic control system 200 to a group of motors during motor time interval 910, and then from a group of sensors to the electronic control system 200 during the sensor time interval 920.

It is important to note several aspects about FIG. 9. First, the group of motors and the group of sensors referred to above consist, respectively, of those motors and of those sensors that are scheduled to exchange data during this particular IO cycle 900. Second, the bus controller 730 could also be programmed so that sensor operations occur before motor operations. However, one benefit to performing motor operations first is evident in an emergency condition where one or more motors needs to be stopped as soon as possible. Third, although IO cycle 900 is shown to involve both motor operations and sensor operations, IO cycles can also involve solely motor operations or solely sensor operations. Lastly, the exemplary IO cycle 900 and its intervals and subintervals will be referred to throughout this disclosure.

Another example of how the bus controller 730 can provide order within an IO cycle is by grouping data writes and grouping data reads separately within time intervals, such as motor time interval 910 and sensor time interval 920. For example, as shown in FIG. 8, the bus controller 730 can allocate bus access time for all motor commands to be written from the electronic control system 200 to the data bus 700 during an initial motor time subinterval 930. As will be described below, the motors can quasi-simultaneously read and actuate upon the motor commands during a subsequent motor time subinterval 940. Similarly, the bus controller 730 can allocate bus access time for sensor readings to be written to the data bus 700 during a preliminary sensor time subinterval 950. Thereafter, the electronic control system 200 and other interested components can read these sensor readings during a latter sensor time subinterval 960.

It can be advantageous for the bus controller 730 to coordinate motors of the RCGS 10 to actuate based on motor commands at the same time. For example, the RCGS 10 can have ten actuation units with each unit having a motor for independently controlling a steering wire of the catheter 406. If the ten motors are actuated at different times, movement of the catheter 406 can be relatively sporadic. Thus one skilled in the art will understand the advantages of actuating all ten motors simultaneously or quasi-simultaneously.

One way for the bus controller 730 to achieve coordinated actuation is to broadcast a synchronization signal to a group of motor nodes connected to the data bus 700 during IO cycles that involve motor time intervals. To illustrate, with continued reference to the exemplary IO cycle 900 in FIG. 9, the electronic control system can write at least one motor command to the data bus 700 during the initial motor time subinterval 930. Also during this initial motor time subinterval 930, the data bus 700 can distribute motor commands from the electronic control system 200 to a local buffer associated with each motor node. The motor nodes can be from a group of motors that are scheduled to actuate in this IO cycle 900. Thereafter, the bus controller 730 can broadcast a synchronization signal 970 to the group of motor nodes that are scheduled to actuate during this particular IO cycle 900. The synchronization signal 970 can indicate the beginning of the subsequent motor time subinterval 940 in which the group of motors are to actuate. In an alternative embodiment, the expiration of a synchronization timer within IO cycle 900 can signal the beginning of the subsequent motor time subinterval 940. In immediate response to either the synchronization signal or the expiration of the synchronization timer, the motors read the motor command stored in their respective local buffers and actuate simultaneously or quasi-simultaneously. In this way, the data bus 700 in effect "releases" all motor commands to the motors at the same time, allowing for coordinated actuation. In effect, the receipt of a synchronization signal controls the moment when motors interact with the process environment of the RCGS 10.

It should be noted that if the data bus 700 is "active," the data bus 700 can be capable of distributing motor commands, sensor readings, and the like without any preconfigured mapping or routing scheme between connected nodes. However, if the data bus 700 is "passive," the data bus 700 can be preconfigured to "distribute" motor commands, sensor readings, and the like according to a routing or mapping scheme.

Figure 10:
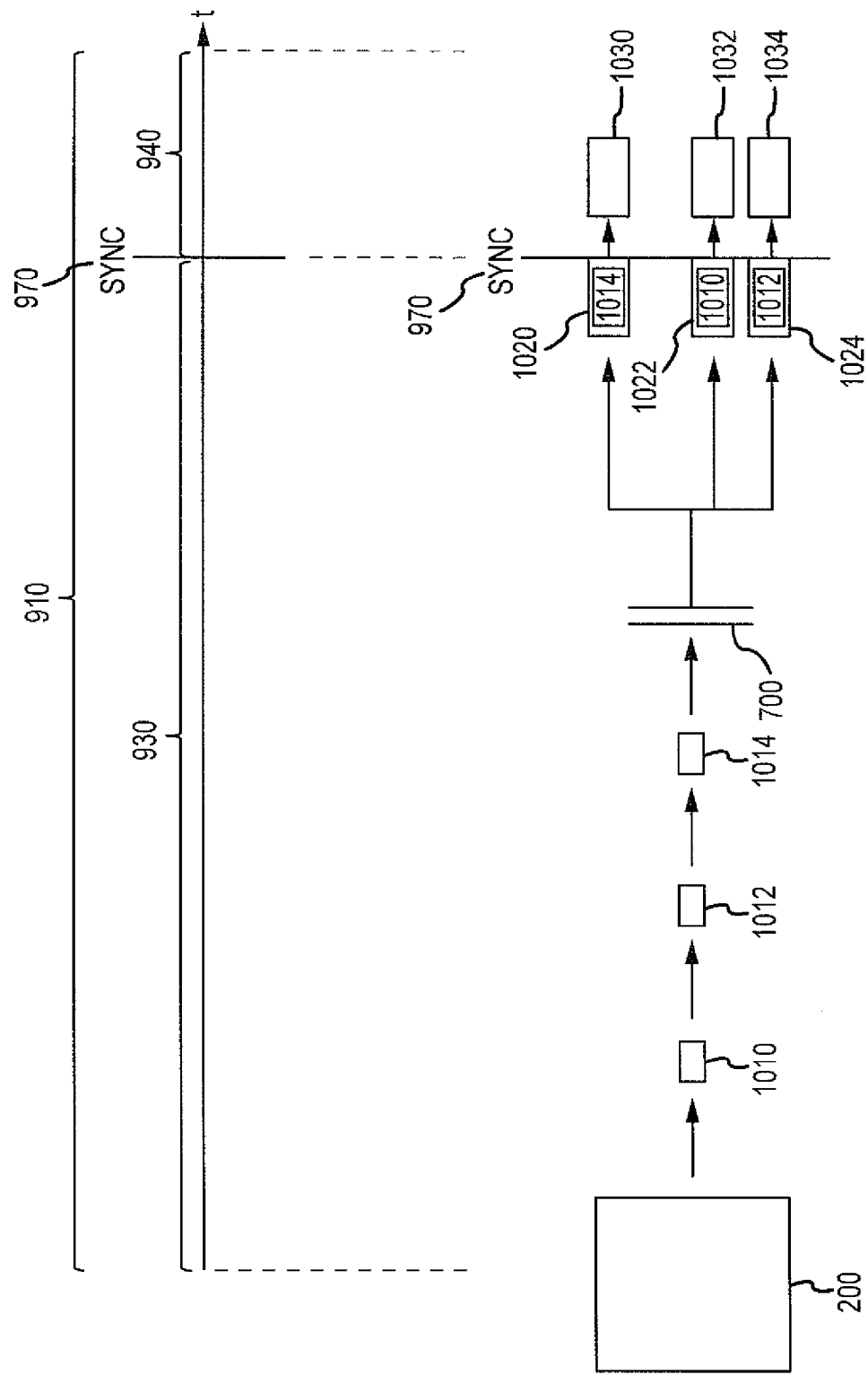
FIG. 10 represents an embodiment in which an electronic control system can send motor commands to a data bus for further distribution to motor nodes and for eventual coordinated actuation upon a synchronization signal.

One embodiment of the motor time interval 910 that facilitates quasi-simultaneous motor actuation is shown in more detail in FIG. 10. As with all timelines in the figures, FIG. 10 is not drawn to scale. During the initial motor time subinterval 930, the electronic control system 200 can transmit to the data bus 700 motor commands 1010, 1012, and 1014 for three motors acting as constituents of a group of motors scheduled to perform operations during this IO cycle. The data bus 700 can further distribute these motor commands 1010, 1012, and 1014 to local buffers 1020, 1022, and 1024 of motors 1030, 1032, and 1034. During the subsequent motor time subinterval 940, which can in one embodiment be triggered by the bus controller 730 broadcasting a synchronization signal 970, the motors 1030, 1032, and 1034 can actuate upon the motor commands 1010, 1012, and 1014 at the same time. Although the subsequent motor time subinterval 940 is depicted as a period of time during which the motors 1030, 1032, and 1034 can actuate, the motors 1030, 1032, and 1034 together actuate in immediate response to the synchronization signal 970.

The data bus 700 can receive sensor readings in several different ways during the sensor time intervals 920. In one embodiment where the bus controller 730 is based on CANopen, the bus controller 730 can write requests for sensor readings to a group of sensor nodes scheduled to report data in a particular IO cycle. In response, the sensor nodes can write the sensor readings to the data bus 700. Thereafter, the electronic control system 200 and other components interested in the sensor readings can read the sensor readings from the data bus 700. In another embodiment where the bus controller 730 is based on a GPIO, the bus controller 730 or other bus interface mechanisms can write sensor readings from a group of sensor nodes to the data bus 700 at every recurrence of an IO cycle that involves the sampling of the group of sensor nodes.

To illustrate basic operation of the data bus 700 in the RCGS 10, an example will be described in which deflection of the joystick 110 used to control the catheter 406 results in the motors manipulating the steering wires to move the catheter 406—all within milliseconds. Continued reference will be made to the IO cycle 900 shown in FIG. 9.

As a user deflects the joystick 110, values measured by sensors positioned alongside the joystick 110 begin to change. Bus interface mechanisms can then write the sensor readings of these joystick 110 sensors to the data bus 700 during the next IO cycle in which these sensors are scheduled to perform operations. Given the critical nature of the joystick 110, the IO cycle to which these sensors are assigned will likely be programmed to recur within milliseconds. After the sensor readings are written to the data bus 700 during a preliminary sensor time subinterval, the electronic control system 200 can read the sensor readings from the data bus 700 in a latter sensor time subinterval.

After the electronic control system 200 has read the sensor readings from the data bus 700, the electronic control system 200 can compute motor commands based on the sensor readings. One such motor command can, for example, be directed to the motor 614 shown in FIG. 6. At the next IO cycle in which a group of motors controlling the steering wires are scheduled to perform operations, the electronic control system 200 can transmit the motor commands to the data bus 700 during the initial motor time subinterval 930. Also during this initial motor time subinterval 930, the data bus 700 can distribute these motor commands to the local buffer of each respective motor. Given the critical nature of catheter 406 movement, the IO cycle to which this group of motors is assigned will likely be programmed to recur within milliseconds. As stated previously, the initial motor time subinterval 930 can be triggered by the expiration of an IO cycle timer specific to IO cycle 900. Next, the synchronization signal 970 can trigger this group of motors to actuate simultaneously or quasi-simultaneously based on the motor commands previously distributed to their respective local buffers. In this way, the bus controller 730 can coordinate the group of motors to manipulate respective steering wires to guide the catheter 406 as desired by the user.

This sequence of events can happen many times as the joystick 110 is being deflected. This means that many IO cycles involving the joystick 110 sensors and many IO cycles involving the steering wire motors (if not part of the same IO cycle) can occur during joystick 110 deflection. As this sequence of events is occurring, the encoders (e.g., the encoder 616 in FIG. 6) and other sensors measuring similar attributes of the steering wire motors (e.g., the motor 614 in FIG. 6) can be intermittently providing closed-loop feedback to the electronic control system 200. The feedback is intermittent if the IO cycle(s) to which these encoders are assigned perform operations between each successive group of motor operations. This closed-loop feedback can, for example, indicate the actual positions of the steering wire motors. Moreover, if the motor 614 is not positioned as expected based on the encoder 616 feedback, the electronic control system 200 can transmit compensatory motor commands in the next IO cycle involving steering wire motor operations.

Only cyclical (i.e., periodic) operations on the data bus 700 have been described. With cyclical operations, bus load at any given point in time is known because the periods with which each IO cycle recurs are known. However, the bus coordinator 730 can also utilize some acyclical operations to optimize the data bus 700 since bus access time is not used when the need is not present. Acyclic operations can be used to communicate, for example, event-driven conditions that are not normally present in the RCGS 10.

Both cyclic and acyclic operations are performed within IO cycles, but acyclic operations are not performed periodically, as are cyclic operations. As explained in the example with the steering wire motor and the fan blowing air over the electronic control system 200, some (cyclic) operations can recur periodically, but with different respective frequencies. However other (acyclic) operations can only occur, for example, when triggered by certain events or requests from other devices.

Figure 11:
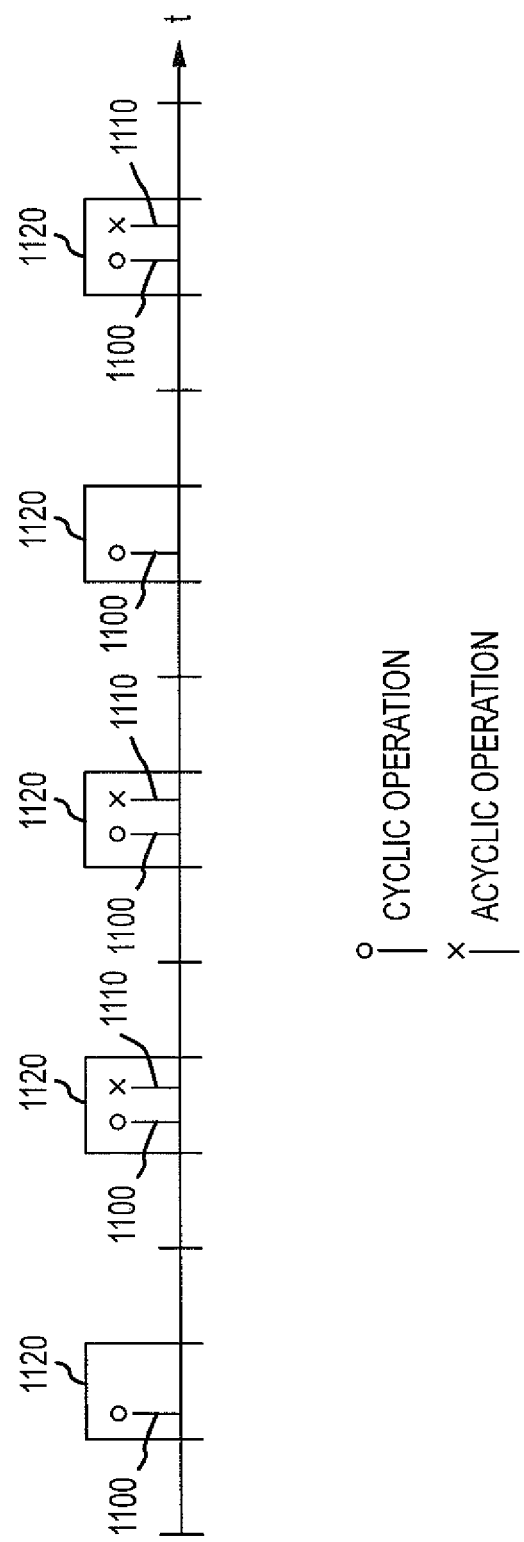
FIG. 11 is a timeline illustrating the difference between acyclic and cyclic operations performed on a data bus.

With reference to FIG. 11, an exemplary timeline of bus access is shown with a cyclic operation 1100 and an acyclic operation 1110 occurring within IO cycles 1120. The cyclic operation 1100 is performed during every IO cycle 1120 to which it is assigned. The acyclic operation 1110 does not occur periodically with every IO cycle 1120 to which it is assigned. In an alternative embodiment, acyclic operations are not assigned to specific IO cycles. Instead, the bus controller 730 can as needed generate an IO cycle for the acyclic operation or assign the acyclic operation to an existing IO cycle.

In one example of an acyclic operation, such as acyclic operation 1110 in FIG. 11, the electronic control system 200 can provide haptic feedback to a user of the joystick 110. Haptic feedback involves imposing counteracting forces on the joystick 110 as it is deflected by the user. The counteracting forces signal to the user that the tip of the catheter 406 has contacted or is about to contact an object. The tip of the catheter 406 can be instrumented with a force sensor configured to transmit a sensor reading during the next occurrence of an IO cycle to which the force sensor is assigned. Since the sensor reading is not transmitted periodically, the sensor reading can be an acyclic message to the electronic control system 200 indicating such contact or imminent contact. The electronic control system 200 can read this data from the data bus 700 and compute a motor command for at least one motor disposed along the joystick 110. During the next IO cycle to which such motor operations are assigned, the electronic control system 200 can then transmit the motor command to the data bus 700. Upon receipt of the motor command from the data bus 700, the motor disposed along the joystick 110 can then actuate the motor command, signaling to the user that the tip has contacted or is about to contact an object.

Some of the operations described thus far, such as motor actuation, for example, are synchronous. All of the operations described thus far, though, can be referred to as being generally synchronous. The operations are generally synchronous because motor operations occur together during motor time intervals and because sensor operations occur together during sensor time intervals.

In addition to generally synchronous operations, it can be helpful in various embodiments to perform at least some operations asynchronously. Asynchronous operations can occur at any point in time, without respect to time intervals or IO cycles. Asynchronous operations, therefore, are not assigned to specific IO cycles or time intervals. For example, an asynchronous motor operation occurs immediately rather than waiting for the next motor time interval or the next IO cycle. With reference to FIG. 9, this means that the asynchronous motor operation could occur, for example, during the preliminary sensor time subinterval 950. As a further example, an asynchronous sensor operation occurs immediately rather than waiting for the next sensor time interval or the next IO cycle. With reference to FIG. 10, this means that the asynchronous sensor operation could occur, for example, during the time interval shown by 70-80 milliseconds, where no IO cycle is scheduled to occur.

Both cyclic and acyclic operations are different from asynchronous operations because asynchronous operations need not necessarily occur during respective motor and sensor time intervals of an IO cycle. Generally synchronous operations, even those that are acyclic, only occur during respective motor and sensor time intervals and hence must wait for the respective motor or sensor time interval of the next IO cycle to which it is assigned.

In the example above, it is also contemplated that haptic feedback could be configured for asynchronous operation. Yet a user would not likely recognize a difference in receiving the counteracting force on the joystick 110 milliseconds earlier (because asynchronous operations do not wait until the next time window).

Asynchronous operations can be of particular value when used to communicate event-driven conditions. For example, it can be desirable to communicate the existence of an error state in the RCGS 10 as it occurs, as opposed to waiting for the next sensor time interval, even if it is just milliseconds away. In addition, error states can be infrequent and unpredictable, so it can be wasteful to allocate recurring bus access time for transmitting the status of a potentially nonexistent error state. If the event sensor corresponding to the asynchronous operation is important, the bus controller 730 recognizes this and provides prompt access to the data bus 700, whether during an IO cycle or not. Time can either be built into IO cycles to account for asynchronous operations or the priority of the asynchronous message can simply allow it to take precedence over other scheduled operations.

The data bus 700 can combine generally synchronous operations (both cyclic and acyclic) and asynchronous operations to provide order and predictability to the way in which data is exchanged on the data bus 700. Different interests depending on the application can be considered when initially configuring these operations on the bus 700. A few examples of competing interests include the priority of certain communication paths, safety margins for bus error states, guaranteed reaction times for events, and cycle times for closed control loops.

Figure 12:
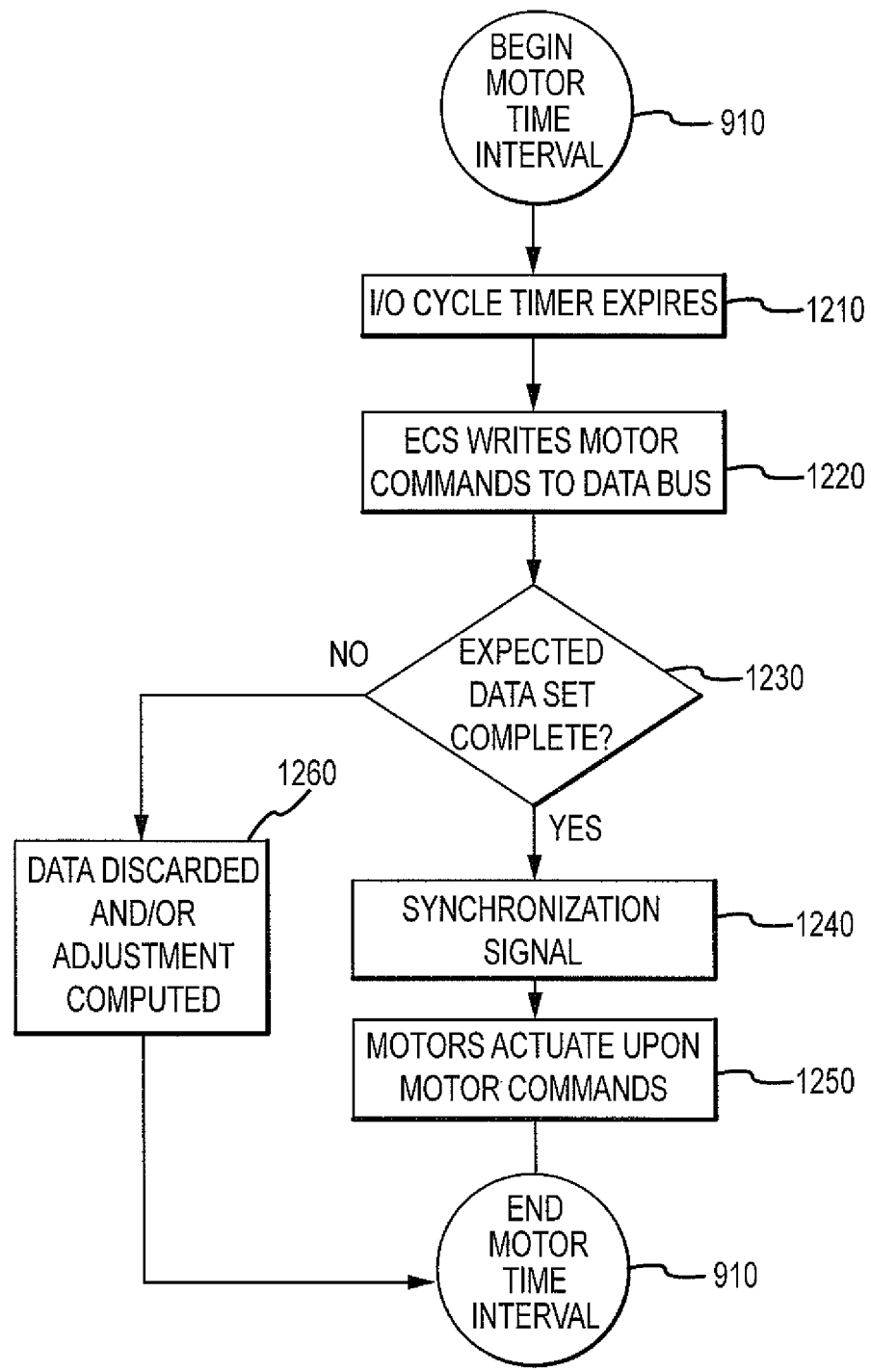
FIG. 12 is a schematic diagram showing the operation of one embodiment of a data bus that prevents incomplete sets of data from being transmitted through the data bus.

In one embodiment, the bus controller 730 can be configured to prevent incomplete sets of data from being transmitted and received over the data bus 700. The operation of this embodiment during the motor time interval 910 is depicted in the flow diagram of FIG. 12. In step 1210, an IO cycle timer expires, prompting an IO cycle with the motor time interval 910 to begin performing its thread of operations. Then, in step 1220, the electronic control system 200 writes motor commands to the data bus 700 for distribution to the local buffers of the motors scheduled to actuate in this IO cycle. Next, in step 1230, the bus controller 730 performs a verification operation on the data bus 700 to ensure that all expected data has been successfully and completely transmitted to the data bus 700. If motor commands are complete, the bus controller 730 can, in one embodiment, broadcast a synchronization signal in step 1240. In response, all the motors assigned to this IO cycle actuate in step 1250 based on the motor commands provided to their respective local buffers.

If, however, in step 1230 the expected data set is not complete, the motors are prevented from actuating in step 1260. For example, if ten motors are scheduled to actuate in this motor time interval 910 and the bus controller 730 recognizes that only nine motor commands are provided to the data bus 700, the bus controller 730 can prevent the motor commands from being distributed to the local buffers of the motors. Discarding the motor commands if any portion is missing can prevent the motors from actuating in uncoordinated fashion and can prevent the RCGS 10 from entering an incomplete state. After the motor commands are discarded, motor time period 910 ends. Alternatively, the electronic control system 200 or the bus controller 730 can be configured to adjust or compensate for incomplete data sets and manage the system response thereto, instead of simply discarding the incomplete data set. One skilled in the art will recognize that a similar preventative measure can be taken for other sets of data, such as, for example, sensor readings.

Through the use of the data bus 700 and the bus controller 730, the RCGS 10 can facilitate communication between many components every few milliseconds. For some components, this entails frequently recurring exchanges of data. For others, the exchange of data can be triggered, for example, by internal events, remote requests from other devices, and other internal timers. Based on this exchange of data from the various components over the bus 700, the electronic control system 200 can be constantly aware of the current state of the RCGS 10.

The electronic control system 200 can make ongoing adjustments as needed, transmitting data over the data bus 700 to the motors used to actuate the RCGS 10, particularly motors controlling the steering wires. One such adjustment can involve, for example, slowing, accelerating, or stopping motors. Likewise, if motors receive motor commands, attempt to perform the commands, and encoders measure that the motors are not where they are expected, the electronic control system 200 can compensate for this in its next transmission of motor commands.

It will be appreciated that in addition to the methodologies of the disclosed invention as described above, another aspect of the present disclosure involves the structure of the electronic control system 200, the bus controller 730, and the data bus 700 configured to optimize bus traffic and to provide order to the way in which components of a system exchange data. It will be further appreciated that the methodology and constituent steps thereof performed and carried out by the electronic control system 200, the bus controller 730, and the data bus 700, which were described in great detail above, apply to this aspect of the disclosure with equal force. Therefore, the description of the methodology as set forth above will not be repeated in its entirety.

Although a number of embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the disclosure as defined in the appended claims.

What is claimed is:

1. A method for scheduling operations on a data bus used to exchange data throughout a system having a plurality of motors and a plurality of sensors, the method comprising:
    determining respective bus access frequencies for a plurality of motors and a plurality of sensors, each bus access frequency being indicative of a frequency with which a respective one of the plurality of motors or a respective one of the plurality of sensors requires access to a data bus;
    providing a plurality of repeating input/output (IO) cycles, wherein at least one of the plurality of motors or at least one of the plurality of sensors accesses the data bus during each of the plurality of IO cycles;
    defining a respective cycle period, for each of the plurality of IO cycles, between respective recurrences of each of the plurality of IO cycles; and
    assigning at least one of the plurality of motors and at least one of the plurality of sensors to at least one of the plurality of IO cycles according to respective bus access frequencies determined for the at least one of the plurality of motors and the at least one of the plurality of sensors;
    wherein access to the data bus by motors and sensors assigned to one of the plurality of IO cycles excludes access to the data bus by motors and sensors assigned to each other IO cycle of the plurality of IO cycles;
    wherein a priority of each of the plurality of IO cycles is determined by the respective cycle periods of each of the plurality of IO cycles and an IO cycle having a lower priority is blocked from accessing the data bus while an IO cycle having a higher priority is accessing the data bus; and
    wherein access is granted to an IO cycle with a higher priority when two or more IO cycles request access to the data bus at substantially the same time.

2. The method of claim 1 further comprising performing a plurality of motor operations before performing a plurality of sensor operations in an IO cycle having both motor operations and sensor operations.

3. The method of claim 2, wherein each of a plurality of motor commands are written to the data bus before any of the plurality of motor commands are read from the data bus and each of a plurality of sensor readings are written to the data bus before any of the plurality of sensor readings are read from the data bus.

4. The method of claim 1 further comprising actuating at least two of the plurality of motors quasi-simultaneously in response to a transmission of a synchronization signal.

5. The method of claim 1, wherein at least two of the plurality of motors that perform similar functions are assigned to a same IO cycle.

6. The method of claim 1, wherein at least two of the plurality of sensors that measure similar attributes are assigned to a same IO cycle.

7. The method of claim 1, wherein at least two of the plurality of motors control at least one steering wire, the at least one steering wire further controlling a tip of a catheter, wherein actuation of at least two of the plurality of motors controlling the steering wires is performed quasi-simultaneously.

8. A method for operating a system using a data bus to exchange data throughout a plurality of motors and a plurality of sensors, the method comprising:
    receiving at least one motor command transmitted to a data bus, the at least one motor command used to control at least two of a plurality of motors;
    distributing the at least one motor command to the at least two motors during one of a plurality of IO cycles, each IO cycle defining a repeating duration of time with a defined frequency during which one or more of at least one of the at least two motors and at least one of the plurality of sensors accesses said data bus;
    actuating the at least two motors in response to a synchronization signal that is different from the at least one motor command, the synchronization signal received during the one IO cycle, the at least two motors actuating based on the at least one motor command; and
    receiving at least one sensor reading from at least one of a plurality of sensors.

9. The method of claim 8, wherein at least one of the plurality of sensors transmits at least one sensor reading to the data bus cyclically and at least one of the plurality of sensors transmits at least one sensor reading to the data bus acyclically.

10. The method of claim 8 further comprising:
checking the at least one motor command transmitted to the data bus for completeness; and
discarding the at least one motor command if a portion of the at least one motor command is missing.

11. The method of claim 8 further comprising storing the at least one motor command in a buffer before actuating at least two of the plurality of motors in response to the synchronization signal.

12. The method of claim 8, wherein the motor commands are based at least in part on the at least one sensor reading received from the at least one of the plurality of sensors.

13. The method of claim 8, wherein at least two of the plurality of motors control at least one steering wire, the at least one steering wire further controlling a tip of a catheter, wherein actuation of at least two of the plurality of motors controlling the steering wires is performed quasi-simultaneously.

14. The method of claim 8, wherein the one IO cycle includes access to the data bus by both a sensor and a motor.

15. A system of sensors and motors using a data bus to exchange data throughout the system, the system comprising:
an electronic control system for computing at least one motor command;
a bus controller configured to allow the at least one motor command to be distributed during one of a plurality of IO cycles, each IO cycle defining a repeating duration of time with a defined frequency during which one or more of a sensor and a motor accesses said data bus;
a plurality of motors capable of actuating based on the at least one motor command;
a plurality of sensors for measuring at least one sensor reading from a system, wherein the electronic control system is configured to receive the at least one sensor reading; and
a data bus for exchanging data between the electronic control system, the plurality of motors, and the plurality of sensors, wherein the plurality of motors actuate based on the at least one motor command in response to a synchronization signal received during the one IO cycle that is different from the at least one motor command.

16. The system of claim 15, wherein at least one of the plurality of sensors transmits the at least one sensor reading to the data bus cyclically and at least one of the plurality of sensors transmits the at least one sensor reading to the data bus acyclically.

17. The system of claim 15, wherein the bus controller is configured to check the at least one motor command for completeness and to prevent at least one of the plurality of motors from actuating if a portion of the at least one motor command is missing.

18. The system of claim 15, wherein the electronic control system is configured to read at least one sensor reading from the data bus during a second subinterval of a sensor time interval, the at least one sensor reading having been written to the data bus during a first subinterval of the sensor time interval.

19. The system of claim 15, wherein at least two of the plurality of motors control at least one steering wire, the at least one steering wire further controlling a tip of a catheter, wherein actuation of at least two of the plurality of motors controlling the steering wires is performed quasi-simultaneously.

20. The system of claim 15, wherein the electronic control system computes the at least one motor command based at least in part on the at least one sensor reading from at least one of the plurality of sensors.

21. The system of claim 15, wherein the one IO cycle includes access to the data bus by both a sensor and a motor.

22. The system of claim 21, wherein the one IO cycle includes a sensor time interval for exchanging sensor readings on the data bus followed by a motor time interval for exchanging motor commands on the data bus.

* * * * *